US011103548B2

(12) United States Patent
Singh

(10) Patent No.: US 11,103,548 B2
(45) Date of Patent: Aug. 31, 2021

(54) TREATMENT OF ENDOMETRIOSIS, ANGIOGENESIS AND/OR ENDOMETRIAL LESION GROWTH

(71) Applicant: SYNG Pharmaceuticals Inc., Kingston (CA)

(72) Inventor: Vinay K. Singh, Kingston (CA)

(73) Assignee: SYNG PHARMACEUTICALS INC., Kingston (CA)

( * ) Notice: Subject to any disclaimer, the term of this patent is extended or adjusted under 35 U.S.C. 154(b) by 0 days.

(21) Appl. No.: 15/924,964

(22) Filed: Mar. 19, 2018

(65) Prior Publication Data

US 2018/0256670 A1 Sep. 13, 2018

Related U.S. Application Data

(63) Continuation of application No. 14/774,235, filed as application No. PCT/CA2014/050173 on Mar. 5, 2014, now abandoned.

(60) Provisional application No. 61/786,240, filed on Mar. 14, 2013.

(51) Int. Cl.
| | |
|---|---|
| *A61K 38/10* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/08* | (2006.01) |
| *A61K 45/06* | (2006.01) |

(52) U.S. Cl.
CPC .............. *A61K 38/10* (2013.01); *A61K 45/06* (2013.01); *C07K 7/08* (2013.01)

(58) Field of Classification Search
None
See application file for complete search history.

(56) References Cited

U.S. PATENT DOCUMENTS 7,897,568 B2 3/2011 Jia et al.

OTHER PUBLICATIONS

Aguilar et al., "Physiological Pathways and Molecular Mechanisms Regulating Uterine Contractility," Human Reproduction Update, Nov.-Dec. 2010, vol. 16 (6), pp. 725-744.
Ahmad et al., "Gamma-Synuclein and the Progression of Cancer," The FASEB Journal, Jun. 2007, vol. 21 (13), pp. 3419-3430.
Arici et al., "Endometriosis and Inflammation in Infertility," Annals of the New York Academy of Sciences, Dec. 2004, vol. 1034 (1), pp. 300-315.
Belotti et al., "Matrix Metalloproteinases (MMP9 and MMP2) Induce the Release of Vascular Endothelial Growth Factor (VEGF) by Ovarian Carcinoma Cells, Implications for Ascites Formation," Cancer Research, Sep. 2003, vol. 63 (17, pp. 5224-5229.
Bruening et al., "Synucleins are Expressed in the Majority of Breast and Ovarian Carcinomas and in Preneoplastic Lesions of the Ovary,"Cancer,May 2000, vol. 88 (9), pp. 2154-2163.
Bulun, "Endometriosis," The New England Journal of Medicine, Jan. 2009, vol. 360 (3), pp. 268-279.
Bulun et al., "Role of Estrogen Receptor-β in Endometriosis," Seminars in Reproductive Medicine, Aug. 2012, vol. 30 (1), pp. 39-45.
Collette et al., "Evidence for an Increased Release of Proteolytic Activity by the Eutopic Endometrial Tissue in Women with Endometriosis and for Involvement of Matrix Metalloproteinase-9," Human Reproduction, Jun. 2004, vol. 19 (6), pp. 1257-1264.
Endometriosis-Prevention, WebM D, accessed on Jan. 26, 2017, available online at http://www.webmd.com/women/endometriosis/endometriosisprevention, 4 pages.
Giudice et al., "Endometriosis," Lancet, Nov. 2004, vol. 364 (9447), pp. 1789-1799.
Hayrabedyan et al., "FGF-1 and S100A13 Possibly Contribute to Angiogenesis in Endometriosis," Journal of Reproductive Immunology, Oct. 2005, vol. 67 (1-2), pp. 87-101.
Jiang et al., "Stimulation of Estrogen Receptor Signaling by Gamma Synuclein," Cancer Research, Jul. 2003, vol. 63 (14), pp. 3899-3903.
Levy et al., "Economic Burden of Surgically Confirmed Endometriosis in Canada," Journal of Obstetrics and Gynaecology Canada, Aug. 2011, vol. 33 (8), pp. 830-837.
Magon, "Gonadotropin Releasing Hormone Agonists, Expanding Vistas," Indian Journal of Endocrinology and Metabolism, Oct. 2011, vol. 15 (4), pp. 261-267.
Matsuzaki et al., "Expression of Estrogen Receptor Alpha and Beta in Peritoneal and Ovarian Endometriosis," Fertility and Sterility, Jun. 2001, vol. 75 (6), pp. 1198-1205.
Medical Dictionary, Prevention, accessed on Jan. 30, 2017, Available online http://medical-dictionary.thefreedictionary.com/prevention, 4 pages.
Murk et al., "Extracellularly Signal-Regulated Kinase Activity in the Human Endometrium: Possible Roles in the Pathogenesis of Endometriosis," The Journal of Clinical Endocrinology & Metabolism, Sep. 2008, vol. 93 (9), pp. 3532-3540.
Nisolle et al., "Early-Stage Endometriosis: Adhesion and Growth of Human Menstrual Endometrium in Nude Mice," Fertility and Sterility, Aug. 2000, vol. 74 (2), pp. 306-312.
Pitsos et al., "The Role of Matrix Metalloproteinases in the Pathogenesis of Endometriosis," Reproductive Sciences, Aug. 2009, vol. 16 (8), pp. 717-726.
Prince et al., "The Pathogenesis of Endometriosis, Still Searching for Answers,"Obstetrics and Gynaecology Forum, Jan. 2015, vol. 25 (4), pp. 31-38.
Ramesh et al., "Efficacy of Gamma Synuclein Inhibitor, TAT-P12, on Survival of Human Endometriotic Lesions in a Mouse Model," Journal of Reproductive Immunology, May 2012, vol. 94, p. 115.

(Continued)

*Primary Examiner* — Thea D'Ambrosio

(57) ABSTRACT

Synuclein-gamma (SNCG) inhibitors are useful for inhibiting or treating angiogenesis, endometriosis and/or endometrial lesion growth. They also potentiate efficacy of other hormonal agents in treating angiogenesis, endometriosis and/or endometrial lesion growth.

3 Claims, 7 Drawing Sheets

Specification includes a Sequence Listing.

(56) References Cited

OTHER PUBLICATIONS

Rawson, "Prevalence of Endometriosis in Asymptomatic Women," The Journal of Reproductive Medicine, Jul. 1991, vol. 36 (7), pp. 513-515.
Saare et al., "Polymorphisms in MMP-2 and MMP-9 Promoter Regions are Associated with Endometriosis," Fertility and Sterility, Sep. 2010, vol. 94 (4), pp. 1560-1563.
Singh et al., "Elevated Expression of CYP1A1 and Gamma-Synuclein in Human Ectopic (Ovarian) Endometriosis Compared with Eutopic Endometrium," Molecular Human Reproduction, Nov. 2008, vol. 14 (11), pp. 655-663.
The University of Maryland Medical Center, Endometriosis, accessed on Jan. 26, 2017, available online at https://umm.edu/health/medical/reports/articles/endometriosis, 17 pages.
U.S. Appl. No. 14/774,235, Final Office Action dated Sep. 20, 2017.
U.S. Appl. No. 14/774,235, Office Action dated Mar. 1, 2017.
Worley et al., "Endometriosis-Associated Ovarian Cancer, A Review of Pathogenesis," International Journal of Molecular Sciences, Mar. 2013, vol. 14 (3), pp. 5367-5379.
Yoshino et al., "Possible Pathophysiological Roles of Mitogen-Activated Protein Kinases (MAPKs) in Endometriosis," American Journal of Reproductive Immunology, Nov. 2004, vol. 52 (5), pp. 306-311.

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: X is G, A, V, L, I, M, F, W, P or N
<220> FEATURE:
<221> NAME/KEY: VARIANT
<222> LOCATION: (3)..(3)
<223> OTHER INFORMATION: X is S, T, C, Y, N or Q
<220> FEATURE:
<221> NAME/KEY: VARIANT
<222> LOCATION: (4)..(4)
<223> OTHER INFORMATION: X is G, A, V, L, I, M, F, W or P
<220> FEATURE:
<221> NAME/KEY: VARIANT
<222> LOCATION: (7)..(7)
<223> OTHER INFORMATION: X is G, A, V, L, I, M, F, W, P or Q
<220> FEATURE:
<221> NAME/KEY: VARIANT
<222> LOCATION: (9)..(9)
<223> OTHER INFORMATION: X is G, 1, V, L, I, M, F, W, P, S, T, C, Y, N
      or Q
<220> FEATURE:
<221> NAME/KEY: VARIANT
<222> LOCATION: (10)..(10)
<223> OTHER INFORMATION: X is S, T, C, Y, N, Q or K
<220> FEATURE:
<221> NAME/KEY: VARIANT
<222> LOCATION: (11)..(11)
<223> OTHER INFORMATION: X is S, T, C, Y, N, Q or V

<400> SEQUENCE: 1

Gly Asn Asn Leu Leu His Ile Ala Ala Ser Gln Gly
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

Gly Asn Ser Ala Leu His Val Ala Ser Gln His Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Gly Asn Asn Leu Leu His Ile Ala Ala Ser Gln Gly
1               5                   10

<210> SEQ ID NO 4
<211> LENGTH: 12
```

```
<212> TYPE: PRT
<213> ORGANISM: Artificial Sequence
<220> FEATURE:
<223> OTHER INFORMATION: Synthetic Peptide

<400> SEQUENCE: 4

Lys Leu Thr Pro Ala Gly Leu Ala Ile Lys Asn Gly
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Glu Pro Ser Leu Ile His Val Ala Gly Cys Val Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Petpide

<400> SEQUENCE: 6

Gly Asn Ser Ala Val His Val Ala Ser Gln His Gly
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: DISULFIDE
<222> LOCATION: (1)..(1)
<220> FEATURE:
<221> NAME/KEY: DISULFIDE
<222> LOCATION: (5)..(5)
<220> FEATURE:
<221> NAME/KEY: MISC_FEATURE
<222> LOCATION: (8)..(21)
<223> OTHER INFORMATION: D-form of amino acid

<400> SEQUENCE: 7

Cys Asn Gly Arg Cys Gly Gly Lys Leu Ala Lys Leu Ala Lys Lys Leu
1               5                   10                  15

Ala Lys Leu Ala Lys
            20

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Gly Asn Gly Arg Gly
1               5

<210> SEQ ID NO 9
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: DISULFIDE
<222> LOCATION: (1)..(1)
<220> FEATURE:
<221> NAME/KEY: DISULFIDE
<222> LOCATION: (5)..(5)

<400> SEQUENCE: 9

Gly Asn Gly Arg Gly
1               5

<210> SEQ ID NO 10
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 10

Gly Tyr Gly Arg Lys Lys Arg Arg Gln Arg Arg Gly Asn Ser Ala
1               5                   10                  15

Leu His Val Ala Ser Gln His Gly
            20

<210> SEQ ID NO 11
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 11

Gly Tyr Gly Arg Lys Lys Arg Arg Gln Arg Arg Arg
1               5                   10
```

TREATMENT OF ENDOMETRIOSIS, ANGIOGENESIS AND/OR ENDOMETRIAL LESION GROWTH

CROSS-REFERENCE TO RELATED APPLICATIONS

This application is a continuation of application U.S. Ser. No. 14/774,235, filed Sep. 10, 2015, which is a national stage entry of International Application No. PCT/CA2014/050173, filed Mar. 5, 2014, which claims priority from provisional Application U.S. 61/786,240, filed Mar. 14, 2013, the entire content of all of which is hereby incorporated by reference.

FIELD OF THE INVENTION

The present invention relates to pharmaceutical compositions and their use in treating endometriosis, angiogenesis and/or endometrial lesion growth.

BACKGROUND OF THE INVENTION

Endometriosis:

The uterus is a hollow organ with three layers: outer serous layer, middle muscular myometrium and inner glandular endometrium (Aguilar et al. Hum. Reprod. Update 16: 6: 725-744, 2010). Endometriosis is an estrogen dependent inflammatory disease that is characterized by the growth of endometrium outside of the uterine cavity (Bulun S E. N. Engl. J. Med. 360: 3: 268-279, 2009). Endometrial lesions are found mainly on the peritoneum in the pelvic cavity and the ovaries but they are also found on the fallopian tube and the rectovaginal septum (Giudice et al. Lancet 364: 9447: 1789-1799, 2004). Common symptoms of endometriosis include chronic pain, dyspareunia, dysmennorhea and infertility (Giudice et al. Lancet 364: 9447: 1789-1799, 2004). Approximately 6-10% of women of reproductive age in North America are thought to have endometriosis and 35-50% of women with pelvic pain, infertility or both are diagnosed with endometriosis. Although endometriosis has been characterized since 1860 and is relatively widespread, little is known about the etiology or pathogenesis of this disease (Giudice et al. Lancet 364: 9447: 1789-1799, 2004).

There are several theories that attempt to explain the pathogenesis of endometriosis. The most widely accepted theory is retrograde menstruation, which suggests that sloughed endometrial tissue in menstrual fluid enters the peritoneal cavity via the fallopian tube (Giudice et al. Lancet 364: 9447: 1789-1799, 2004). The endometrial tissue then is believed to attach to the epithelium of the peritoneal cavity, establish a blood supply and proliferates. There are, however, specific genetic, environmental and immunological factors that are implicated in the pathogenesis of endometriosis (Giudice et al. Lancet 364: 9447: 1789-1799, 2004).

Diagnosis of endometriosis is performed by visualization of the lesions by laparoscopy (Giudice et al. Lancet 364: 9447: 1789-1799, 2004) however, it is challenging due to the lack of appropriate non-invasive tests and varying symptoms (Rawson J M. J. Reprod. Med. 36: 7: 513-515, 1991). In 2011, endometriosis was estimated to cost approximately $4043 per patient per year in Canada (Levy et al. J Obstet Gynaecol Can. 33: 8: 830-837, 2011). Current treatments mainly include GnRH agonists and oral contraceptives to lower the levels of estrogen in patients (Giudice et al. Lancet 364: 9447: 1789-1799, 2004). Other treatment options include hormone therapy, pain killers and surgical resection of the endometrial lesion (Giudice et al. Lancet 364: 9447: 1789-1799, 2004). None of these treatments, however, are suitable for long term therapy due to adverse side effects and high recurrence rates. In addition, these treatments often do not support pregnancy. Since endometriosis affects women of reproductive age, and none of the current long term therapeutic options are viable with pregnancy, there is a niche to develop a therapeutic option compatible with female fecundity.

Gamma Synuclein (γ-Synuclein) in Endometriosis:

Synuclein-gamma (SNCG) is an oncogene and is overexpressed in advanced and metastatic cancers. SNCG is also a chaperone protein in the (Hsp)-based multiprotein chaperone complex for stimulation of ligand-dependent estrogen receptor (ER)-α signaling and stimulates hormone-responsive cell proliferation. Gamma synuclein, originally referred to as breast cancer-specific gene 1, is a 123 amino acid long protein that is encoded by the γ-synuclein gene (SNCG) (Ahmad et al. FASEB J. 21: 13: 3419-3430, 2007). γ-synuclein is normally found in parts of the brain, heart, skeletal muscle, liver, pancreas and recently endometrium (Ahmad et al. FASEB J. 21: 13: 34193430, 2007; Singh et al. Mol. Hum. Reprod. 14: 11: 655-663, 2008). Most research on γ-synuclein has focused on its role in neuronal development, neurodegenerative disorders and cancer; however the association of γ-synuclein in endometriosis was recently discovered. Singh et al assessed the levels of γ-synuclein in ectopic (abnormal) and eutopic (normal) endometrial tissue samples by using immunohistochemistry (Singh et al. Mol. Hum. Reprod. 14: 11: 655-663, 2008). They observed that ectopic endometrium expressed significantly more γ-synuclein than eutopic endometrium (Singh et al. Mol. Hum. Reprod. 14: 11: 655-663, 2008).

γ-synuclein could have a variety of roles in the pathogenesis of endometriosis. It is found to increase 30 the transcriptional activity of estrogen receptor a (ER-α) (Jiang et al. Cancer Res. 63: 14: 3899-3903, 2003), which is an important mediator in the development of endometriosis, as the disease is estrogen dependent (Bu]un et al. Semin. Reprod. Med. 30: 1: 39-45, 2012). Matsuzaki et al. also found that both eutopic and ectopic endometrium expressed significantly more ERα mRNA than ER-β (Matsuzaki et al. Fertil. Steril. 75: 6: 1198-1205, 2001).

γ-synuclein has also been found to induce the expression of matrix metalloproteinases (MMPs) (Jiang et al. Cancer Res. 63: 14: 3899-3903, 2003). In particular, it is found to induce the expression of MMP2 and MMP9 (Pitsos et al. Reprod. Sci. 16: 8: 717-726, 2009) Matrix metalloproteinases are important enzymes that help degrade extracellular matrix (ECM) (Pitsos et al. Reprod. Sci. 16: 8: 717-726, 2009). In order to grow, a lesion needs to attach and invade the extracellular matrix and subsequently obtain its own blood supply through a process called angiogenesis (Nisolle et al. J. Fertil. Steril. 74: 2: 306-312, 2000). The first steps to lesion attachment and angiogenesis is the degradation of ECM (Pitsos et al. Reprod. Sci. 16: 8: 717-726, 2009). Studies have found that MMP-9 secretion is higher in the endometriotic cells of women with endometriosis than those without (Collette et al. Hum. Reprod. 19: 6: 1257-25 1264, 2004). The same study also found that proteolytic activity of the endometrial tissue is higher in women with endometriosis, and some of this increase in activity may be attributed to MMP-9 and other MMPs (Collette et al. Hum. Reprod. 19: 6: 1257-1264, 2004). It was also found that patients with severe forms of endometriosis had polymorphisms in their MMP-9 gene, which may correlate to MMP-9 overexpression (Saare et al. Fertil. Steril. 94: 4: 1560-1563, 2010). MMP-9 and MMP2 also induce the release of vascular endothelial growth factor (VEGF), which plays a key role in angiogenesis (Belotti et al. Cancer Res. 63: 17: 5224-5229, 2003).

In addition to aiding invasion, angiogenesis and growth, γ-synuclein also has a role in controlling inflammation, which is associated with both the chronic pain and infertility that is related to endometriosis (Halis G and Arici A. Ann. N.Y. Acad. Sci. 1034: 1: 300-315, 2004). γ-synuclein has been found to activate mitogen-activated protein kinases (MAPKs), specifically extracellular signal-related kinases1/2(ERK1/2) (Ahmad et al. FASEB J. 21: 13: 3419-3430, 2007). MAPKs play a pivotal role as intracellular messengers in various pathways that are involved in the pathogenesis of endometriosis, including inflammation (Yoshino et al. Am. J. Reprod. Immunol. 52: 5: 306-311, 2004). They also seem to play a role in angiogenesis by acting as one of the intracellular messengers for fibroblast growth factor-1 (FGF-1) (Hayrabedyan et al. J. Reprod. Immunol. 67: 1-2: 87-101, 2005). Recent studies have shown that endometrial stromal cells have higher levels of MAPKs as compared to normal stromal cells (Yoshino et al. Am. J. Reprod. Immunol. 52: 5: 306-311, 2004). ERK1/2 phosphorylation in particular was found to be upregulated in women with endometriosis, which was found to enhance the survival of endometrial stromal cells (Murk et al. J. Clin. Endocrinol. Metab. 93: 9: 3532-3540, 2008).

SUMMARY OF THE INVENTION

It has now been found that y-synuclein (SNCG) inhibitors are useful in the inhibition or treatment of endometriosis, angiogenesis or endometrial lesion growth. Such SNCG inhibitors may interact with SNCG and reduce SNCG-mediated cell proliferation, for example by reducing the number of available ER-α receptors.

Thus, there is provided a use of a γ-synuclein (SNCG) inhibitor for inhibition or treatment of endometriosis, angiogenesis, endometrial lesion growth or a combination thereof.

There is also provided a use of a γ-synuclein (SNCG) 10 inhibitor for preparation of a medicament for inhibition or treatment of endometriosis, angiogenesis, endometrial lesion growth or a combination thereof.

There is also provided a pharmaceutical composition for inhibition or treatment of endometriosis, angiogenesis, endometrial lesion growth or a combination thereof, the composition comprising a γ-synuclein (SNCG) inhibitor in an amount effective to inhibit or treat endometriosis, angiogenesis or endometrial lesion growth.

There is also provided a commercial package comprising a γ-synuclein (SNCG) inhibitor and instructions for its use to inhibit or treat endometriosis, angiogenesis, endometrial lesion growth or a combination thereof.

There is also provided a method of inhibiting or treating endometriosis, angiogenesis, endometrial lesion growth or a combination thereof, the method comprising administering to a subject a γ-synuclein (SNCG) inhibitor in an amount effective to inhibit or treat endometriosis, angiogenesis, endometrial lesion growth or a combination thereof.

There is also provided a use of a synuclein-gamma (SNCG) inhibitor for potentiating an anti-angiogenesis agent or a hormonal agent in the inhibition or treatment of endometriosis, angiogenesis, endometrial lesion growth or a combination thereof.

In one aspect, the y-synuclein (SNCG) inhibitor comprises a synthetic peptide, portion thereof or mimetic thereof. Particularly useful peptides in the present invention comprise the amino acid sequence, $GX_1X_2X_3LHX_4AX_5X_6X_7G$ (SEQ ID NO: 1), where $X_1$ is G, A, V, L, I, M, F, W, P or N; $X_2$ is S, I, C, Y, N or Q; $X_3$ is G, A, V, L, I, M, F, W or P; $X_4$ is G, A, V, L, I, NI, F, W, P or Q; $X_5$ is G, A, V, L, I, M, F, W, P, 5, T, C, Y, N or Q; $X_6$ is 5, T, C, Y, N, Q or K; $X_7$ is 5, I, C, Y, N, Q or V; or a portion or mimetic thereof. More preferred is ST011 peptide GNSALHVASQHG (SEQ ID NO: 2) or a portion or mimetic thereof.

Another aspect of the present invention relates to pharmaceutical compositions comprising a synthetic peptide as described above, portion thereof or mimetic thereof, which inhibits angiogenesis, endometriosis and/or endometrial lesion growth. Preferred compositions have a formula of Y-Z or Q-Y-Z, wherein Y comprises the peptide as described above, portion thereof or mimetic thereof; Z comprises a compound linked to Y that enhances the performance of Y; and in embodiments comprising Q, Q comprises another compound linked to Y-Z which also enhances performance of the Q-Y-Z composition. Q may be identical to Z or different from Z. Exemplary Z or Q compounds include, but are not limited to a targeting agent, a second agent for treatment of cell proliferation, an agent which enhances solubility, absorption, distribution, half-life, bioavailability, stability, activity and/or efficacy, or an agent which reduces toxicity or side effects of the composition.

Pharmaceutical compositions of the present invention 5 may further comprise an anti-angiogenesis agent or a hormonal agent.

Another aspect of the present invention relates to a method for inhibiting SNCG-mediated endometrial cell proliferation comprising administering to the endometrial cells a peptide or portion thereof, a Y-Z or Q-Y-Z composition, or a mimetic of these which inhibits SNCG-mediated endometrial cell proliferation and/or inhibits angiogenesis, endometriosis and endometrial lesion growth.

Another aspect of the present invention relates to a method for potentiating activity of an anti-angiogenesis agent or a hormonal agent comprising administering to the endometrial cells a peptide or portion thereof, a Y-Z or Q-Y-Z composition, or a mimetic of these which inhibits SNCG-mediated endometrial cell proliferation and/or inhibits angiogenesis, endometriosis and endometrial lesion growth. In this method, the peptide or portion thereof, a Y-Z or Q-Y-Z composition, or a mimetic of these which inhibits SNCG-mediated endometrial cell proliferation and/or inhibits angiogenesis, endometriosis and endometrial lesion growth and the hormonal drug may be administered to the endometrial cells simultaneously as a single pharmaceutical composition, at the same time in separate pharmaceutical compositions or at different times. Preferred drugs used in this method are hormonal treatments.

The present invention is particularly useful in mammalian subjects including humans, dogs, cats, horses, cows, pigs, mice, rats, guinea pigs, etc. Use of the present invention in humans is of particular note.

DETAILED DESCRIPTION OF THE INVENTION

Figure 1:
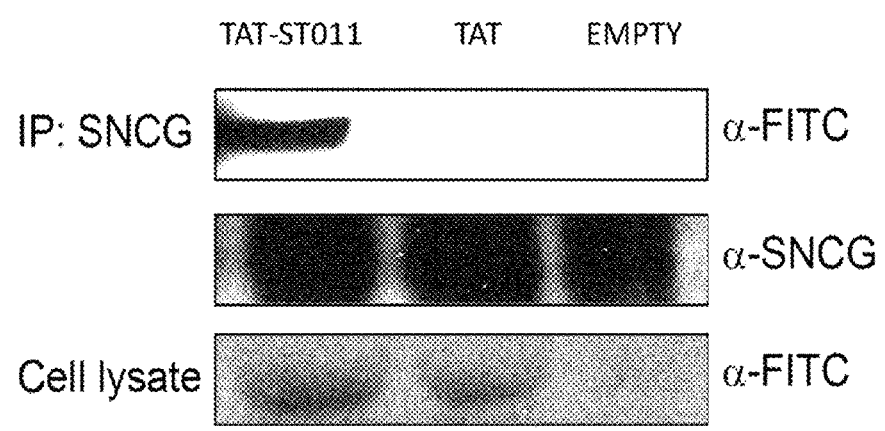
FIG. 1 provide results of binding of ST011 peptide GNSALHVASQHG (SEQ ID NO: 2) with SNCG protein in a co-immunoprecipitation reaction.

The inventors have now identified synthetic peptides, portions thereof or mimetics thereof which associate with SNCG and inhibit angiogenesis, endometriosis and/or endometrial lesion growth. The prominent expression of SNCG in multiple types of cells causing abnormal growth is indicative of these peptides, portions thereof or mimetics thereof having a broad effect in cells positive for SNCG. Synthetic peptides, portions thereof or mimetics thereof are known from U.S. Pat. No. 7,897,568 issued Mar. 1, 2011, the entire contents of which are herein incorporated by reference.

In this description, the synthetic peptide GNSALHVASQHG (SEQ ID NO: 2) is referred to herein as the ST011 peptide.

By "portion thereof" it is meant to be inclusive of peptides exhibiting similar biological activities to the ST011 peptide described herein but which, (1) comprise shorter fragments of the 12 residue ST011 peptide. Accordingly, in a preferred embodiment, by portion thereof, it is meant a peptide of the present invention comprising part, preferably at least 5 to 7 amino acid residues, of the N terminus and/or C terminus of ST011 peptide.

By "synthetic", as used herein it is meant that the peptide or portion thereof is prepared synthetically either by chemical means or recombinantly.

Further, it will of course be understood, without the intention of being limited thereby, that a variety of substitutions of amino acids in the disclosed ST011 peptide is possible while preserving the structure responsible for its interaction with SNCG and its inhibition of angiogenesis, endometriosis and/or endometrial lesion growth. For example, substitution of one or more amino acids of the ST011 peptide with one or more amino acids of the ST011 consensus sequence(s) such as set forth in Table 1 is expected to produce a peptide with similar biological activity to the ANK peptide and thus is encompassed within the scope of the present invention.

TABLE 1

| | |
|---|---|
| S1011-like 1 | GNNLLHIAASQG (SEQ ID NO: 3) |
| S1011-like 2 | KLIPAGLAIKNG (SEQ ID NO: 4) |
| S1011-like 3 | EPSLIHVAGCVG (SEQ ID NO: 5) |
| ST011-like 4 | GNSAVHVASQHG (SEQ ID NO: 6) |
| ST11 peptide | GNSALHVASQHG (SEQ ID NO: 2) |

Conservative substitutions are also described in the patent literature, as for example, in U.S. Pat. No. 5,264,558. It is thus expected, for example, that interchange among non-polar aliphatic neutral amino acids, glycine, alanine, praline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could possibly be made, as could substitutions among the charged basic amino acids, lysine and arginine. Substitutions among the aromatic amino acids, including phenylalanine, histidine, tryptophan and tyrosine would also likely be possible. In some situations, histidine and basic amino acids lysine and arginine may be substituted for each other. These sorts of substitutions and interchanges are well known to those skilled in the art and encompassed within the scope of the ST011 peptide of the present invention.

Active principles comprising the active peptides, portions thereof or mimetics thereof are used in a therapeutically effective amount, singly or in combination. A therapeutically effective amount will depend on the species of subject, on body weight and may also be influenced by individual reaction to the active principles. A therapeutically effective amount is any amount that will successfully inhibit or treat endometriosis, angiogenesis, endometrial lesion growth or a combination thereof in a given subject. In general, the active principles may be used in a daily dosage between 0.0001 mg/kg and 10,000 mg/kg based on weight of the subject. The best daily dosage regime and overall treatment duration is within the abilities of the patient physician to determine for any given subject.

Also preferred for use in the present invention to interact with SNCG and inhibit angiogenesis, endometriosis and endometrial lesion growth are compositions with a formula of Y-Z or Q-Y-Z. In these compositions Z is linked to Y and/or Q is linked to Y-Z via any acceptable binding means and selected based upon selection of Z or Q. Examples of acceptable binding means include, but are in no way limited to, covalent binding, noncovalent binding, hydrogen binding, antibody-antigen recognition and ligand binding. In compositions with the formula Y-Z or Q-Y-Z, Y comprises ST011 peptide or a portion thereof or mimetic thereof; Z comprises a compound linked to Y that enhances the performance of Y; and in embodiments comprising Q, Q may be identical to Z or different from Z and also enhances performance of the compound Q-Y-Z.

Exemplary Z or Q compounds include, but are not limited to, a targeting agent, a second agent for treatment of cancer or endometriosis, an agent which enhances solubility, absorption, distribution, half-life, bioavailability, stability, activity and/or efficacy, or an agent which reduces toxicity or side effects of the compound. By targeting agent it is meant to include agents that direct the composition to the endometriotic lesions as well as agents which enhance or increase entry of the composition into the lesions itself.

Exemplary targeting agents of Z and/or Q include, but are in no way limited to, antibodies and active fragments thereof such as, for example, Fab fragments, peptides, hormones, vitamins, lectins, saccharides, carbohydrates and other ligands that have affinity for cells of interest and/or aid in transport into cells of interest. Preferably, the targeting agent does not influence pharmacokinetics of Y, the Y-Z or Q-Y-Z composition and/or the delivery vehicle.

Examples of targeting peptides useful in these compositions include, but are not limited to, the TAT peptide derived from the HIV-1 TAT protein which facilitates intracellular delivery of proteins and small colloidal particles; the antennapedia protein from Drosophila; the VP22 protein from the herpes simplex virus; transportan and polyarginine; the RGD motif; and the NGR peptide (CNGRCGGklaklakklak-lak-NH2 (Disulfide bridge: 1-5) (SEQ ID NO: 7)). The NGR peptide binds an aminopeptidase (CD13) isoform expressed in tumor blond vessels. Peptides containing the Asn-Gly-Arg (NGR) motif, including both linear GNGRG (SEQ ID NO: 8) and disulfide-bridged CNGRC (SEQ ID NO: 9), have been disclosed to be useful for delivering various viral particles and anti-tumor compounds, such as chemotherapeutic drugs, apoptotic peptides, cytokines, cytotoxic drugs, proapoptotic peptides, and tumor necrosis factor (TNF), to tumor blood vessels (Ellerby et al. Nature Medicine 1999 5:1032; Colombo et al. J. Biol. Chem. 2002 277 (49):47891; Van Hensbergen et al. Binchem. Pharmacol. 2002 63(5):897 (2002); Plesniak et al. Protein Science 2004 13:1988; Curnis et al. Cancer Research 2002 62:867; Curnis et al. J. Clin. Invest. 2002 110(4):475). Exemplary targeting peptides useful in these compositions of the present invention are also described in Schwartz and Zhang (Current Opinion in Molecular Therapeutics 2000 2:162-167), teachings of which are herein incorporated by reference in their entirety.

Alternatively, Y of the Y-Z or Q-Y-Z compositions of the present invention can be conjugated with a hydrophilic polymer such as, but not limited to, polyethylene glycol (PEG) to improve stability and longevity in circulation, to improve permeability into tumor vasculature and interstitial tumor space, and to improve longevity once reaching the interstitial space.

Alternatively, Y of the Y-Z or Q-Y-Z compositions of the present invention can be chemically conjugated to the Fc domain of human gamma immunoglobulin (IgG) or to albumin.

Cell penetrating peptides (CPPs) or peptide transduction domains (PTDs) can also be attached to Y of the Y-Z or Q-Y-Z compositions of the present invention to enhance intracellular delivery. Exemplary CPPs include Tat PTD derived from the HIV Tat protein, Antennapedia (also known as Antp or penetratin), VP22 (a herpes virus protein), model amphipathic peptide (MAP), transportan, transportan-10, KALA, and Pep-1.

Further, vector molecules such as lytic peptides, pH-sensitive polymers or swellable dendritic polymers can be attached to Y of the Y-Z or Q-Y-Z compositions of the present invention as a targeting agent to enhance endosomal escape if internalization is via endocytosis (Torchilin and Lukyanov (2003) Drug Discovery Today 8(6): 259-266).

Many of these targeting agents are commercially available and can be readily linked to Y of the Y-Z or Q-Y-Z compositions of the present invention.

By "mimetic", as used herein, it is meant to be inclusive of peptides, which may be recombinant, and peptidomimetics, as well as small organic molecules, which exhibit similar or enhanced interaction with SNCG and inhibition of angiogenesis, endometriosis and endometrial lesion growth. These include peptide variants which comprise conservative amino acid substitutions relative to the sequences of the ST011 peptides exemplified herein and peptide variants which have a high percentage of sequence identity with the ST011 peptide exemplified herein. By high percentage of sequence identity it is meant a peptide which shares at least 60%, more preferably at least 65%, more preferably at least 70%, more preferably at least 75%, more preferably at least 80%, more preferably at least 85%, more preferably at least 90%, more preferably at least 95%, and more preferably at least 99% sequence identity with ST011 peptide or an exemplified ST011 peptide or portion thereof. For peptides sharing sequence identity with a portion of the ST011 peptide or the exemplary ST011-like peptides exemplified herein, it is preferred that a higher sequence identity be shared with either the N-terminus or the C-terminus of the peptide. Variant peptides can be aligned with the reference peptide or portion thereof to assess percentage sequence identity in accordance with any of the well-known techniques for alignment. For example, a variant peptide greater in length than a reference peptide is aligned with the reference peptide using any well-known technique for alignment and percentage sequence identity is calculated over the length of the reference peptide, notwithstanding any additional amino acids of the variant peptide, which may extend beyond the length of the reference peptide. A variant peptide shorter in length than the reference peptide is aligned with the reference peptide at the region of shared homology, i.e. the C terminus, N terminus or the central region of the reference peptide. Preferred variants include, but are not limited to, peptides comprising one or more D amino acids, which are equally effective but less susceptible to degradation in vivo, and cyclic peptides. Cyclic peptides can be circularized by various means including but not limited to peptide bonds, lactam rings, depsicyclic terminal residues (i.e. a disulfide bond) and/or N-terminal to C-terminal head-to-tail cyclization.

The stability of ST011 peptides and variants thereof of the present invention can also be enhanced by modifications to the peptide or variant including, but not limited to, acetylation, glycosylation, amidation, and/or addition of unnatural amino acids such as p-amino and a-trifluoromethyl amino acids to the ST011 peptide or variant thereof.

As used herein, the term "peptidomimetic" is intended to include peptide analogs that serve as appropriate substitutes for the ST011 peptide, in interacting with SNCG and inhibiting angiogenesis, endometriosis and endometrial lesion growth. The peptidomimetic must possess not only similar chemical properties, e.g. affinity to SNCG, but also efficacy and function. That is, a peptidomimetic exhibits function(s) of ST011 peptide, without restriction of structure. Peptidomimetics of the present invention, i.e. analogs of a ST011 peptide, include amino acid residues or other moieties which provide the functional characteristics described herein. Peptidomimetics and methods for their preparation and use are described in Morgan et al. 1989, "Approaches to the discovery of non-peptide ligands for peptide receptors and peptidases," In Annual Reports in Medicinal Chemistry (Vuirick, F. J. ed), Academic Press, San Diego, Calif., 243-253.

Mimetics of the present invention may be designed to have a similar structural shape to ST011 peptide but have enhanced activities. For example, conformationally restricted moieties such as a tetrahydroisoquinoline moiety may be substituted for a phenylalanine, while histidine bioisoteres may be substituted for histidine to decrease first pass clearance by biliary excretion. Peptidomimetics of the present invention may also comprise peptide backbone modifications. Analogues containing amide bond surrogates are frequently used to study aspects of peptide structure and function including, but not limited to, rotational freedom in the backbone, intra- and intermolecular hydrogen bond patterns, modifications to local and total polarity and hydrophobicity, and oral bioavailability. Examples of isosteric amide bond mimics include, but are not limited to, ψ[CH$_2$S], ψ[CH$_2$NH], ψ[CSNH$_2$], ψ[NHCO], ψ[COCH$_2$] and ψ[(E) or (Z)CH═CH].

Identification of the activity of the ST011 peptides also permits molecular modeling based on these peptides for design, and subsequent synthesis, of small organic molecules that interact with SNCG and inhibit angiogenesis, endometriosis and endometrial lesion growth. These small organic molecules mimic the structure and activity of the ST011 peptide. However, instead of comprising amino acids, these small organic molecules comprise bioisosteres thereof, substituents or groups that have chemical or physical similarities, and exhibit broadly similar biological activities.

Bioisosterism is a lead modification approach used by those skilled in the art of drug design and shown to be useful in attenuating toxicity and modifying activity of a lead compound such as the ST011 peptide of SEQ ID NO: 2, of the ST011 consensus peptide depicted in Table 3. Bioisosteric approaches are discussed in detail in standard reference texts such as The Organic Chemistry of Drug Design and Drug Action (Silverman, R B, Academic Press, Inc. 1992 San Diego, Calif., pages 19-23). Classical bioisosteres comprise chemical groups with the same number of valence electrons but which may have a different number of atoms. Thus, for example, classical bioisosteres with univalent atoms and groups include, but are not limited to: CH$_3$, NH$_2$, OH, F and Cl; Cl, PH$_2$ and SH; Br and i-Pr; and I and t-Bu. Classical bioisosteres with bivalent atoms and groups include, but are not limited to: —CH$_2$— and NH; O, S, and Se; and COCH$_2$, CONHR, CO$_2$R and COSR. Classical bioisosteres with trivalent atoms and groups include, but are not limited to: CH═ and N═; and P═ and As═. Classical bioisosteres with tetravalent atoms include, but are not limited to: C and Si; and ═C+═, ═W═ and ═P+═. Classical bioisosteres with ring equivalents include, but are not limited to: benzene and thiophene; benzene and pyridine; and tetrahydrofuran, tetrahydrothiophene, cyclopentane and pyrrolidine. Nonclassical bioisosteres still produce a similar biological activity, but do not have the same number of atoms and do not fit the electronic and steric rules of classical isosteres. Exemplary nonclassical bioisoteres are shown as follows.

Nonclassical Biosteres

1. Carbonyl group

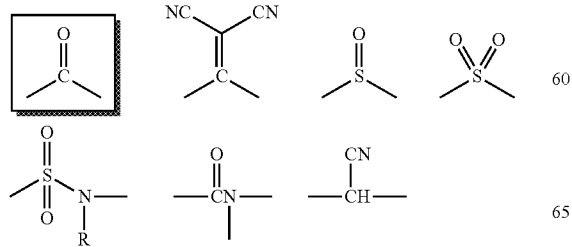

2. Carboxylic acid group

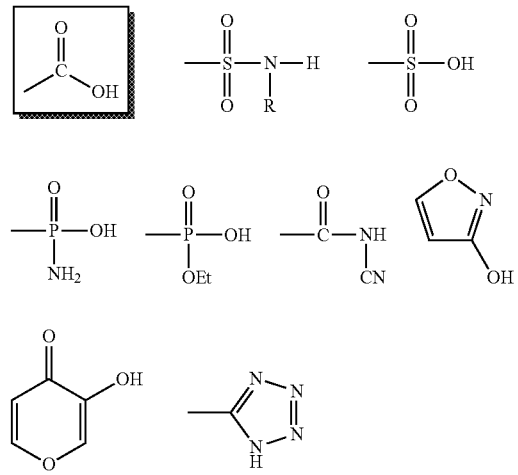

3. Hydroxy group

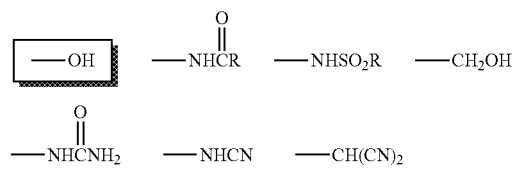

4. Catachol

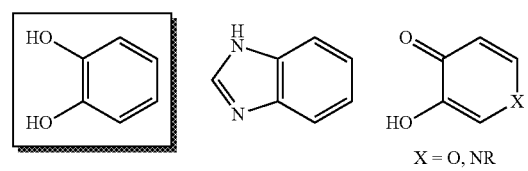

5. Halogen

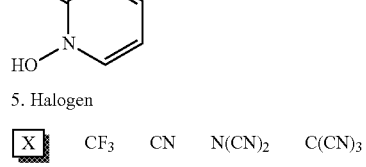

6. Thioether

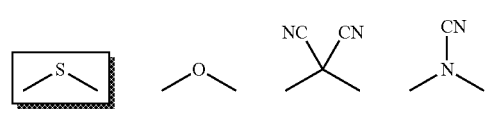

7. Thiourea

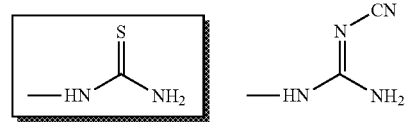

8. Azomethine

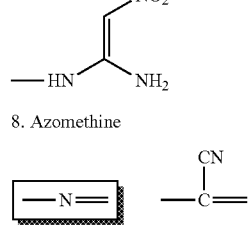

9. Pyridine

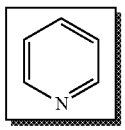 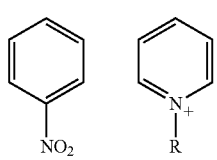 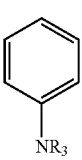

10. Spacer group

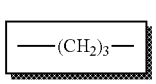 

11. Hydrogen

Additional bioisosteric interchanges useful in the design of small organic molecule mimetics of the present invention include ring-chain transformations.

A peptide or portion thereof, Y-Z or Q-Y-Z composition or mimetic thereof of the present invention is preferably formulated with a vehicle pharmaceutically acceptable for administration to a subject, preferably a human, in need thereof. Methods of formulation for such pharmaceutical compositions are well known in the art and taught in standard reference texts such as Remington's Pharmaceutical Sciences, Mack Publishing Co., Easton, Pa., 1985. A pharmaceutical composition of the present invention may comprise a single peptide or portion thereof, a Y-Z or Q-Y-Z composition, or a mimetic of these which interacts with SNCG and inhibit angiogenesis, endometriosis and endometrial lesion growth. These pharmaceutical compositions may be administered alone or in combination with a second agent a hormonal agent. For example, a pharmaceutical composition of the present invention comprising an ST011 peptide or portion thereof or mimetic thereof, can be administered to a subject in combination with a hormonal drug. Hormonal drugs, such as, but not limited to Gonadotropin-Releasing Hormone (GnRH) Agonists and Antagonists. Gonadotropin-Releasing Hormone (GnRH) Agonists and Antagonists are often used as first line hormonal agents in the treatment of endometriosis.

A preferred formulation for use in pharmaceutical compositions of the present invention is complexing the peptide or mimetic thereof or Y-Z or Q-Y-Z composition with a lipid. Also preferred as a formulation is encapsulation of the peptide or mimetic thereof or Y-Z or Q-Y-Z composition or mimetic thereof in a phospholipid vesicle such as, but not limited to, a liposome. Liposomes containing the peptide or mimetic thereof or Y-Z or Q-Y-Z composition or mimetic thereof of the present invention can be prepared in accordance with any of the well-known methods such as described by Epstein et al. (Proc. Natl. Acad. Sci. USA 82: 3688-3692 (1985)), Hwang et al. (Proc. Natl. Acad. Sci. USA//: 4030-4034 (1980)), EP 52,322, EP 36,676; EP 88,046; EP 143,949; EP 142,641; Japanese Pat. Appl. 83-118008, and EP 102,324, as well as U.S. Pat. Nos. 4,485,045 and 4,544,545, the contents of which are hereby incorporated by reference in their entirety. Preferred liposomes are of the small (about 200-800 Angstroms) unilamellar type in which the lipid content is greater than about 10 mol. Percent cholesterol, preferably in a range of 10 to 40 mol. percent cholesterol, the selected proportion being adjusted for optimal peptide therapy. However, as will be understood by those of skill in the art upon reading this disclosure, phospholipid vesicles other than liposomes can also be used.

Micelles, nanoparticles, injectable polymer implants, gels and other hydrophilic systems, as well as microemulsions currently used or in development as delivery vehicles for peptides can also be used to formulate pharmaceutical compositions in accordance with the present invention.

Any of these formulations of pharmaceutical compositions may further comprise a targeting agent such as described herein for use in Y-Z or Q-Y-Z composition.

When used in this embodiment, the targeting agent is preferably attached to the delivery vehicle (e.g. liposomes, micelles, nanoparticles, injectable polymer implants, gels or other hydrophilic systems).

Another preferred formulation for pharmaceutical compositions of the present invention contains a peptide comprising one or more D amino acids and an aqueous vehicle suitable for intravenous or oral administration. Intravenous formulations expected to be useful as pharmaceutical compositions of the present invention include, but are not limited to, sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g., vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the peptide of the present invention in the required amount in an appropriate solvent with one or a combination of ingredients enumerated above, as required, followed by filter sterilization. Generally, dispersions are prepared by incorporating the peptide of the present invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the peptide) optionally plus any additional desired ingredient from a previously sterile-filtered solution thereof.

Solid dosage forms for oral administration of a peptide or portion thereof, a Y-Z or Q-Y-Z composition, or a mimetic thereof of the present invention include, but are not limited to, ingestible capsules, tablets, pills, lollipops, powders, granules, elixirs, suspensions, syrups, wafers, buccal tablets, troches, and the like. In such solid dosage forms the peptide or portion thereof, the Y-Z or Q-Y-Z composition, or the mimetic thereof is mixed with at least one inert, pharmaceutically acceptable excipient or diluent or assimilable edible carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the peptide or portion thereof, the Y-Z or Q-Y-Z composition, or the mimetic thereof in the pharmaceutical compositions and preparations may, of course, be varied. The amount of the peptide or portion thereof, the Y-Z or Q-Y-Z composition, or the mimetic thereof in such therapeutically useful pharmaceutical compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The peptide or portion thereof, the Y-Z or Q-Y-Z composition, or the mimetic thereof can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the peptide or portion thereof, the Y-Z or Q-Y-Z composition, or the mimetic thereof, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the peptide or portion thereof, the Y-Z or Q-Y-Z composition, or the mimetic thereof, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Peptides and pharmaceutical compositions of the present invention can be administered to a patient with endometriosis to potentiate efficacy of a hormonal drug.

By "potentiating efficacy" it is meant that the hormonal drug is more effective at inhibiting angiogenesis, endometriosis or endometrial lesion in the presence of the ST011 peptide or portion thereof, the Y-Z or Q-Y-Z composition, or the mimetic thereof than in the absence of the ST011 peptide or portion thereof, the Y-Z or Q-Y-Z composition, or the mimetic thereof.

Peptides and pharmaceutical compositions of the present invention can also be administered alone or in combination with a hormonal agent to inhibit angiogenesis, endometriosis and endometrial lesion growth.

Co-administration with a second hormonal drug or agent is expected to improve efficacy of the second hormonal drug, thereby allowing for decreased doses of the second hormnal drug. This decrease in dose is expected to reduce unwanted side effects of the second hormonal drug.

By "inhibit", "inhibiting" or "inhibition" of angiogenesis, endometriosis and/or endometrial lesion growth as used herein, it is meant to encompass prevention of endometriosis or endometrial cell growth.

By "in combination" it is meant to include administration of a single pharmaceutical formulation comprising both the peptide or portion thereof, Y-Z or QY-Z composition or mimetic thereof of the present invention and the hormonal drug as well as administration of two separate pharmaceutical compositions, one comprising the hormonal drug and the other comprising the peptide or portion thereof, Y-Z or Q-Y-Z composition or mimetic thereof of the present invention. When administered separately, the hormonal drug and the peptide or portion thereof, Y-Z or Q-Y-Z composition or mimetic thereof of the present invention can be administered at the same time or at different times.

Accordingly, the peptides and pharmaceutical compositions of the present invention are useful in treating endometriosis. For purposes of the present invention, by "treatment" or "treating" it is meant to encompass all means for controlling angiogenesis, endometriosis or endometrial lesion growth and improving response to hormonal drugs. Thus, by "treatment" or "treating" it is meant to inhibit the survival and/or growth of endometrial lesions, prevent the survival and/or growth of endometrial lesions, decrease the invasiveness of endometrial lesions, decrease the progression of endometrial lesions, and/or facilitate the killing of endometrial lesions and endometriosis. "Treatment" or "treating" is also meant to encompass maintenance of endometrial lesions in a dormant state at their primary site as well as secondary sites. Further, by "treating or "treatment" it is meant to increase the efficacy as well as prevent or decrease resistance to other hormonal drugs.

Peptides and pharmaceutical compositions may be administered by various routes including, but not limited to, orally, intravenously, intramuscularly, intraperitoneally, subcutaneously, topically, rectally, dermally, sublingually, buccally, intranasally or via inhalation. For at least oral administration, it may be preferred to administer a composition comprising a peptide with one or more D amino acids. The formulation and route of administration as well as the dose and frequency of administration can be selected routinely by those skilled in the art based upon the severity of the condition being treated, as well as patient-specific factors such as age, weight and the like.

Pharmaceutical compositions of the present invention may further comprise an anticancer agent. Preferably the anticancer agent is a hormonal therapy.

The interaction of SNCG with the ST011 peptide was examined by various biophysical and cell biological approaches.

In vivo binding of ST011 to SNCG was examined in co-immunoprecipitation (co-IP) experiments (See FIG. 1). MCF7-SNCG cells were treated with FITC tagged GYGRKKRRQRRR (TAT)-ST011 (SEQ ID NO: 10) (lane 1 of FIG. 1), or FITC tagged YGRKKRRQRRR (TAT) alone (SEQ ID NO: 11) (lane 2 of FIG. 1) or no treatment control (lane 3 of FIG. 1). 8 hour after treatment, cell lysates were prepared and IP with anti-SNCG antibody was conducted. The presence of TAT-ST011 in SNCG IP complexes obtained from different treated cells was detected by western blot using anti-FITC antibody. The membrane was subsequently re-probed with anti-SNCG antibody to demonstrate equal amounts of SNCG in IP complexes of MCF7-SNCG cell lysates. The upper panel in FIG. 1 shows that when anti-SNCG IP complexes were probed with FITC antibody, only TAT-ST011 but not TAT alone is found to co-precipitate with SNCG (lane 1) in MCF7-SNCG cells. The lower panel shows the immunoblotting of anti-SNCG and anti-FITC in total cell lysates. Thus, FIG. 1 provides further evidence that SNCG is capable of immunoprecipitating TAT-ST011.

Accordingly, the results of the co-IP experiments depicted in FIG. 1 clearly demonstrate the direct intracellular binding of ST011 peptide to SNCG.

Figure 2:
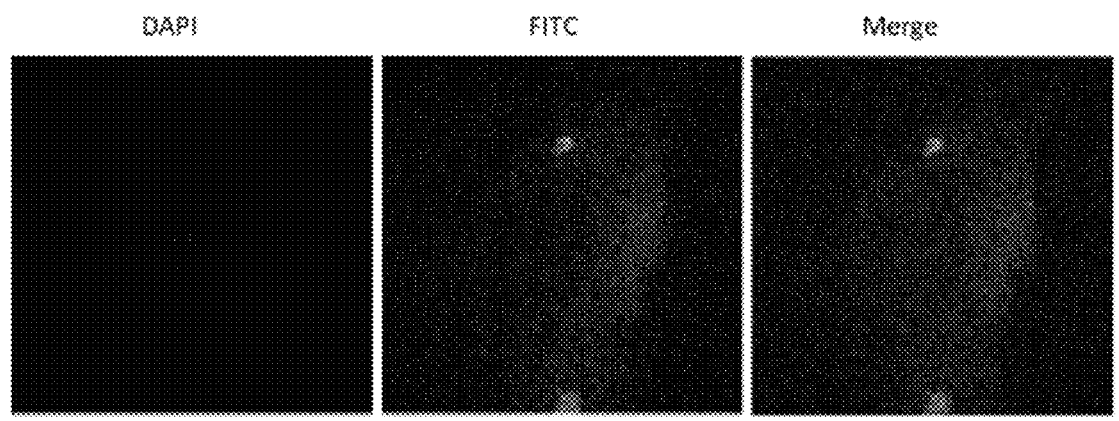
FIG. 2 provide penetration of fluorescently tagged 10 ST011 peptide GNSALHVASQHG (SEQ ID NO: 2) in CRL 7566, a model cell line for endometriosis.

To further examine the utility of the ST011 peptide as a therapeutic tool against angiogenesis, endometriosis and/or endometrial lesion growth, this peptide was further examined to observe its intracellular permeability in endometrial cells. For these experiments, GYGRKKRRQRRR (TAT) tagged GNSALHVASQHG (ST011) (SEQ ID NO: 10) and a control peptide GYGRKKRRQRRR (TAT CTL; SEQ ID NO: 11) were chemically synthesized. Each peptide contained FITC on its N-terminal end. These peptides were dissolved in 2% DMSO in PBS (pH 7.3) and applied directly on the Petri dish containing model cells (CRL 7566 or HUVECs) at required concentrations. Active internalization of peptide was observed using fluorescent microscopy. Three independent experiments were performed with duplicates of each condition. Model cell line for endometriosis, CRL 7566 cells (FIG. 2) received 20 micro molar FITC tagged TAT-ST011. After 6 hours cells were examined under fluorescent microscope. Left panel shows DAPI stained nucleus of the cell, middle panel shows presence of ST011 peptide in the cell due to the presence of fluorescence. Right panel shows a merged image of the left and the middle panel. Thus, FIG. 2 provides further evidence that TAT-ST011 is capable of going inside endometrial cells.

Figure 3:
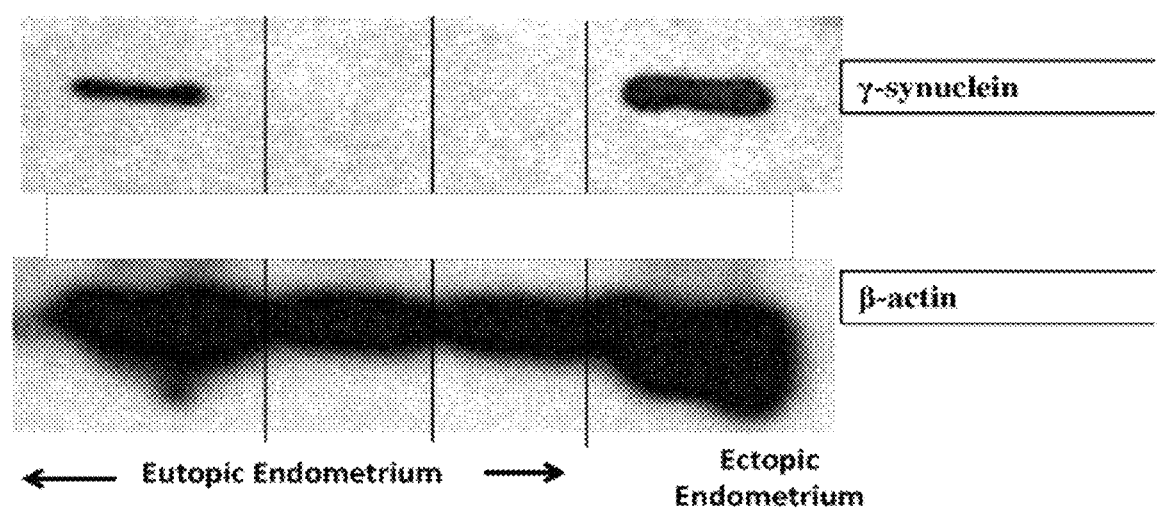
FIG. 3 provides evidence of y-synuclein protein in eutopic (normal) and ectopic (endometriotic) human samples using Western Blot assay. P-actin was used as a loading control.
Figure 4:
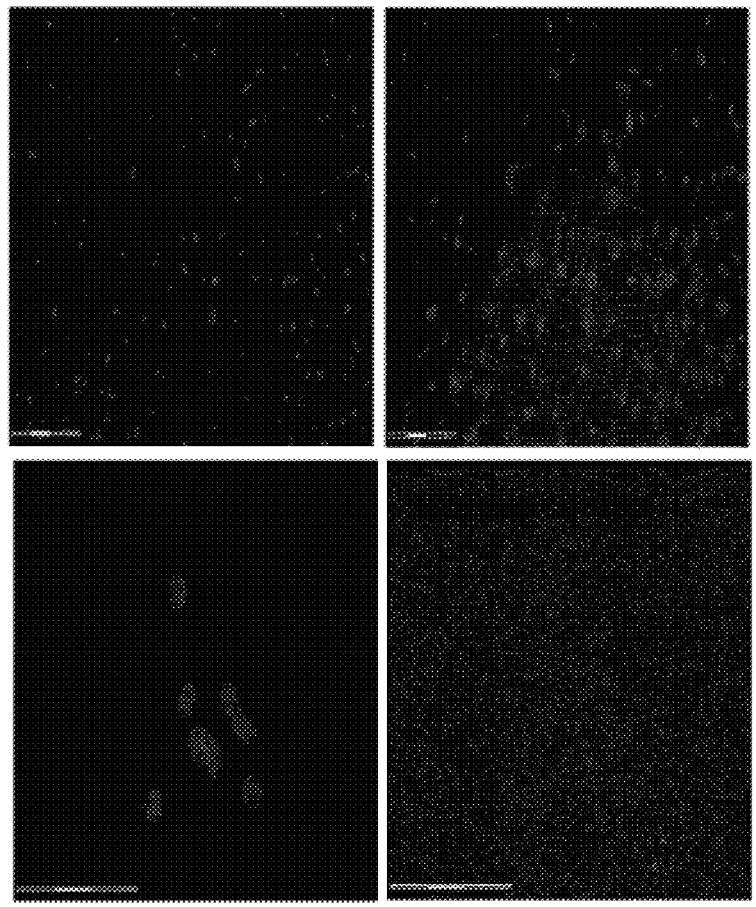
FIG. 4 provides effects of ST011 peptide GNSALHVASQHG (SEQ ID NO: 2) on HUVECs proliferation using WST-1 Proliferation Assay kit manufactured by Roche Diagnostics, IN, USA). ST011 peptide GNSALHVASQHG (SEQ ID NO: 2) inhibited proliferation of HUVECS in a dose dependent manner.

Next evidence is necessary to understand that eutopic and ectopic endometrium contain γ-synuclein protein therapeutic target of ST011 peptide GNSALHVASQHG (SEQ ID NO: 2). Through western blot analysis (FIG. 3) we confirmed increased expression of γ-synuclein in ectopic versus eutopic endometrium (FIG. 3). As seen in FIG. 3, the expression of γ-synuclein in eutopic endometrium was lower or non-existent as compared to ectopic endometrium. β-actin was used as a loading control. Using fluorescent microscopy we validated the outcomes of the western blot experiments and conclusively show presence of γ-synuclein protein in CRL 7566 cells (FIG. 4).

Figure 5:
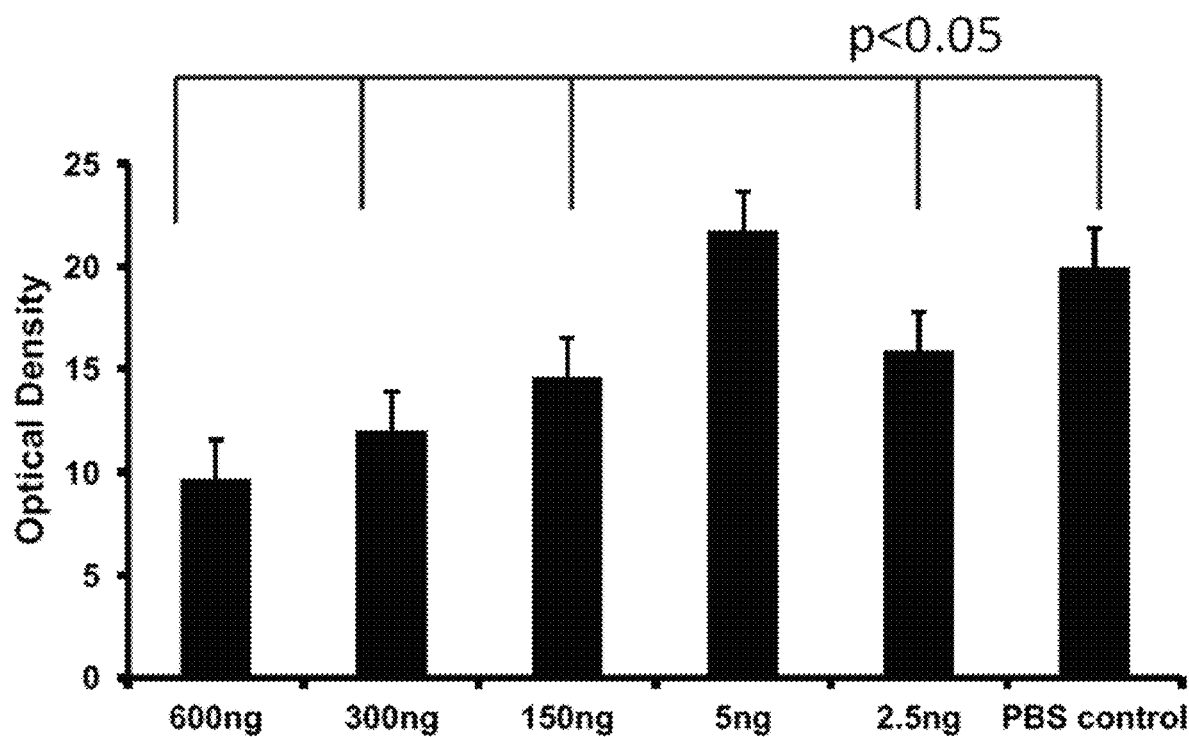
FIG. 5 provides evidence of α-synuclein protein in HUVECs using Immunoflurosence microscopy.

To further demonstrate the function of the ST011 peptide in inhibition of growth of endometriotic lesions and inhibiting angiogenesis, endometriosis and endometrial lesion growth, it was important to show it first in in vitro model. Endothelial cells are an integral part of blood vessels and the proliferation of endothelial cells is extremely important for angiogenesis. Therefore, to assess the role of α-synuclein in endothelial cell proliferation, HUVECs were plated and treated with various concentrations of TATST011 peptide GNSALHVASQHG (SEQ ID NO: 2) ranging from 600 ng/mL to 2.5 ng/mL using PBS as a control. In order to measure the effect of TAT-ST011 peptide GNSALHVASQHG (SEQ ID NO: 2) on HUVEC proliferation a WST-1 proliferation assay was performed. After 48 hours of treatment, TAT-ST011 dose dependently decreased the proliferation of HUVECs ($p \ll 0.05$) (FIG. 5).

Figure 6:
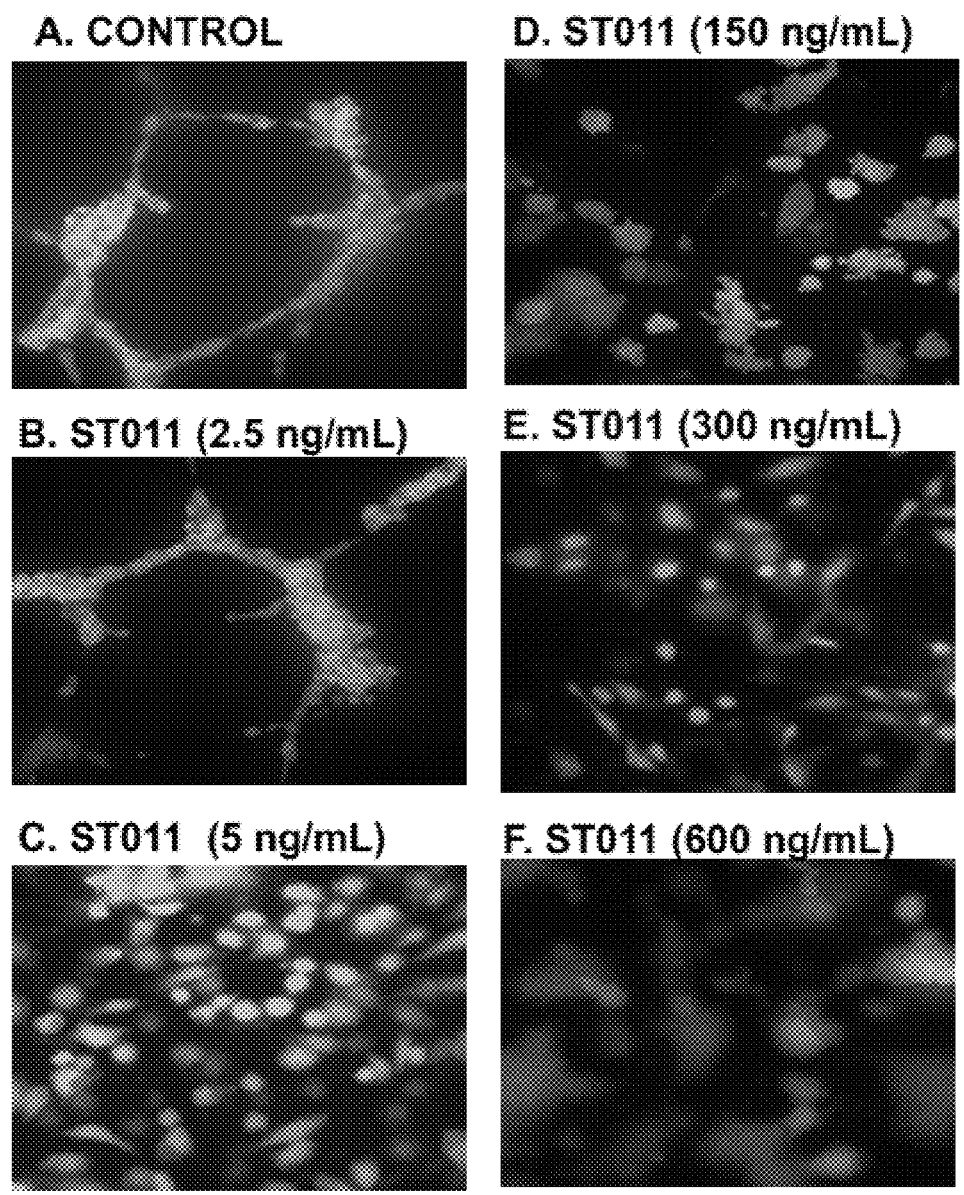
FIG. 6 provides evidence of inhibition of branching of HUVEC cells using matrigel assay in presence of ST011 peptide GNSALHVASQHG (SEQ ID NO: 2). This suggest blockage of angiogenic tube formation of HUVEC cells under various concentrations of ST011 peptide GNSALHVASQHG (SEQ ID NO: 2).

Next, effect of TAT-ST011 peptide GNSALHVASQHG (SEQ ID NO: 2) on angiogenesis and tube formation of HUVEC cell was evaluated. HUVECs were grown on a gel matrix and while being treated with various concentrations of TAT-ST011, confocal microscopy was used to assess tube formation and a dose dependent inhibition of tube formation was observed (FIG. 6). TAT-ST011 in concentrations of 5 ng/mL or higher not only inhibited tube formation but also changed the morphology of the 10 HUVECs. In FIG. 6 the morphology of the HUVECs in the 300 ng/mL and 600 ng/mL indicated that TAT-ST011 treatment caused the cells to lyse.

Figure 7:
FIG. 7 provides evidence of ST011 peptide GNSALHVASQHG (SEQ ID NO: 2) mediated inhibition of human endometriotic lesion growth in a mouse model of endometriosis.

In addition to the above-described in vitro and in vivo assays, efficacy of the peptides of the present invention to inhibit angiogenesis, endometriosis and endometrial lesion growth can be confirmed in a mouse model. Exemplary evidence was obtained to demonstrate inhibition of endometriotic lesion growth. Gross observation of endometriotic lesion growth and vascularization in vivo was performed using an animal model. Mice were sacrificed a week after treatment of TAT-ST011 or saline and were dissected for gross observation of endometriotic lesions and vascularization. The peritoneal cavity of the mice was exposed using surgical tools and the endometriotic lesions were located manually. The lesions of mice treated with saline control were larger and contained more extensive vasculature (FIG. 7, left panel marked control). TAT-ST011 treatment inhibited growth of lesion and prevented the formation of blood vessels to the lesions (FIG. 7, right panel marked ST011 treated).

The ability of ST011 to inhibit endometriosis without effecting fertility can be confirmed in, for example, animal model of endometriosis. For these experiments, humanized animal models of endometriosis first can be treated with ST011 and once endometriosis is inhibited and treatment is stopped, fertility of the animals is tested by mating. Animals give birth to live pups demonstrating no effect of ST011 peptide on the fertility of the animals.

The following non-limiting examples are provided to further illustrate the present invention.

EXAMPLES

Example 1: Cell Culture

HUVECs (Cell Applications, San Diego, Calif., USA) obtained previously from umbilical cord veins were cultured and maintained in T75 flasks containing endothelial cell growth media (Cell Applications, San Diego, Calif., USA). Cells were incubated at 37° C. in a humidified chamber with 5% $CO_2$. HUVECs used in assays were between the third and the seventh passage.

Luminal epithelial cells derived from endometrium adenocarcinomas (CRL-2923, ATCC, Manassas, Va., USA) were cultured and maintained in T75 flasks containing RPMI-1640 (Sigma Chemical Co., St. Louis, Mo., USA) with 5% fetal bovine serum (FBS, Sigma Chemical Co., St.

Louis, Mo., USA) and 1% penicillin and streptomycin (Sigma Chemical Co., St. Louis, Mo., USA). These cells were also incubated at 37° C. in a humidified chamber with 5% $CO_2$. Epithelial cells used for assays were between the second and the fourth passage.

Example 2: STO11 Peptide Synthesis

Peptide was synthesized by solid phase synthesis with amino-terminal acetylation and carboxyl-terminal amidation to mimic the intact protein at a commercial facility. Peptide was purified by reverse phase HPLC using a C18 column (Vydac, Hesperia, Calif.) and lyophilized. The molecular mass of the peptide was verified by matrix-assisted laser desorption ionization time-of-flight (MALDI-TOF) mass spectrometry. Fifty μL aliquots of 1.2 mM STO11 peptide in 10 mM sodium phosphate buffer pH 7.0 were stored at −20° C. until use.

Example 3: Cell Proliferation Assay

HUVECs and epithelial cells were trypsinized, suspended in cultured medium and counted. Approximately 10,000 cells per well were seeded onto a 96 well plate. After allowing 24 hours for attachment in 37° C., the cells were treated with either 600 ng/mL, 300 ng/mL, 150 ng/mL, 5 ng/mL or 2.5 ng/mL of TAT-P12 using phosphate buffer saline (PBS, (Sigma Chemical Co., St. Louis, Mo., USA) as a control. The drug was suspended in RPMI. The plates were incubated in 37° C. for 24 or 48 hours after which 10 μL of WST-1 (Roche, Laval, QC, Canada) was added to each well. The plate was then incubated in 37° C. for another 4 hours. The absorbance of the wells was measured at a wavelength of 490 nm or at 510 nm.

Example 4: Immunocytochemistry

HUVECs were trypsinized and counted. Approximately 50,000 cells were seeded onto glass coverslips and fixed with 70% ethanol for five minutes, followed by a quick hydration phase using deionized water. Cells were blocked with 1% bovine serum albumin (BSA) for one hour and incubated with primary mouse anti-human y-synuclein antibody (Promab Richmond, Calif., USA) for two hours followed by secondary goat anti-mouse tagged ALEXA-594 antibody (Abcam Cambridge, Mass., USA). The slides were coverslipped with 4',6-diamidino-2-phenylindole (DAPI) containing mounting media (Invitrogen, Inc., Carlsbad, Calif., USA).

Example 5: In Vitro Angiogenic Tube Formation

Extracellular matrix gel solution (Cell biolabs inc, San Diego, Calif., USA) had been thawed overnight at 4° C. and approximately 50 pL of ECM gel solution was added to each well of a 96 well plate. The plate was incubated at 37° C. for 1 hour. HUVECs were trypsinized from culture and approximately 20,000 cells were added per well to the ECM containing 96 well plate. Each well was treated with 10 pL of TAT-P12 at a concentration of 600 ng/mL, 300 ng/mL, 150 ng/mL, 5 ng/mL or 2.5 ng/mL. PBS was used as a control. The tube formation was visualized using a spinning disc confocal microscope and the images were stacked together using ImageJ.

Example 6: Western Blots

Proteins were isolated from three eutopic sections and one ectopic endometrial section. Individual samples 25 were homogenized in Tris-buffered saline prepared with nuclease-free water containing 1 mg/mL of aprotinin (Sigma Chemical Co., St. Louis, Mo., USA) then centrifuged at 4° C., 1500 g, for 15 min. The proteins were separated in a 4%-20% tris glycine gel, the gel was run for 110 min 30 at 115V constant. 10 μL of 10 ng/4 protein was loaded per well with 10 μL of loading dye. PVDF western blot membrane was submerged in the transfer buffer for five minutes. The proteins were then transferred to the membrane overnight at 4° C. at 15V. After a ten minutes wash with Tris-buffered saline with tween-20 (TBST) the membrane was blocked with 5% BSA for one hour. The membrane was then incubated with either a 1:5000 dilution of [3-actin conjugated to horseradish peroxidase (control) (Abcam Cambridge, Mass., USA) or 1:1000 dilution of SNCG mouse mAB (Promab Richmond, Calif., USA) for 1-2 hours. The blots were then incubated with an anti-rat horse radish peroxidise conjugated secondary (Cell Signaling Technology, Inc., Danvers, Mass., USA) and both were visualized using Immobilon Western (EMD Millipore, Billerica, Mass., USA) chemiluminescent substrate.

Example 7: In Vivo Mouse Model Mouse Strain

A mouse xenograft model was developed using $Rag2^{-/-}$/ $Il2rg^{-/-}$ double knockout mice on a BalbC background. The mice were housed at Queen's University (Kingston, ON, Canada) and all protocols and procedures were previously approved by the Queen's University Institutional Animal Care Committee.

Implantation of Estrogen Pellet

Since human estrogen is important for the growth of human endometriotic lesions the mice (n=12) had 60-day release 13-estradiol 17-acetate pellets (15 mg/pellet) (Innovative Research of America, Sarasota, Fla., USA) subcutaneously implanted. The mice were anaesthetized with isofluorane (Pharmaceutical Partners of Canada, Richmond Hill, ON, Canada).

Induction of Endometriosis

Five days after the implantation of the estrogen 5 pellet, eutopic endometrium obtained from hysterectomy and endometrial biopsies performed at Kingston General Hospital was implanted in the peritoneal cavity of the mice. The obtained endometrium was cut into equal pieces and washed with PBS. The pieces of endometrium were kept in PBS on ice until the surgeries were performed. The mice were anaesthetized in an isofluorane chamber and a small incision was made in their abdomen. Two to three lesions were adhered on the left side of the peritoneal cavity using Vetbond tissue adhesive (3M, St. Paul, Minn., USA) and one or two pieces were dropped freely in the cavity. The incisions were stapled using 9 mm staples (Becton Dickinson Company, Sparks, Md., USA) which were removed one week later. One of the 12 mice died due to surgical complications 2 days post-surgery.

Treatment

The mice were divided into two groups: saline control (n=5) and TAT-P12 treated (n=6). TAT-P12 was diluted to 20 mg/kg in saline. Mice received daily intraperitoneal injections of 100 uL of TAT-P12 or saline for 21 days using 26 G needles. The injections were administered a week after the induction of endometriosis to allow for the lesion to establish.

Necropsies

Necropsies were conducted one week post treatment. The peritoneal cavities of the mice were exposed for gross anatomical analysis of lesion growth and vascularization.

The novel features of the present invention will become apparent to those of skill in the art upon examination of the detailed description of the invention. It should be understood, however, that the scope of the claims should not be limited by the preferred embodiments set forth in the examples, but should be given the broadest interpretation consistent with the specification as a whole.

The invention claimed is:

1. A method of inhibiting or treating endometriosis, comprising: administering to a subject in need thereof an effective amount of a synthetic peptide selected from the group consisting of SEQ ID NO:2, SEQ ID NO:3, SEQ ID NO:4, SEQ ID NO:5 and SEQ ID NO:6, wherein inhibiting and treating does not encompass prevention of endometriosis.

2. The method according to claim 1, said synthetic peptide is SEQ ID NO:2.

3. The method according to claim 1, wherein the subject is mammalian.

* * * * *